US012582333B1

(12) United States Patent
Berme et al.

(10) Patent No.: US 12,582,333 B1
(45) Date of Patent: Mar. 24, 2026

(54) BODY SWAY MEASUREMENT SYSTEM

(71) Applicant: Bertec Corporation, Columbus, OH (US)

(72) Inventors: Necip Berme, Worthington, OH (US); Murat Kerim Berme, Venice, CA (US); Mohan Chandra Baro, Columbus, OH (US)

(73) Assignee: Bertec Corporation, Columbus, OH (US)

( * ) Notice: Subject to any disclaimer, the term of this patent is extended or adjusted under 35 U.S.C. 154(b) by 0 days.

(21) Appl. No.: 18/587,781

(22) Filed: Feb. 26, 2024

Related U.S. Application Data

(63) Continuation-in-part of application No. 17/836,935, filed on Jun. 9, 2022, now Pat. No. 11,911,147, which is a continuation-in-part of application No. 17/141,014, filed on Jan. 4, 2021, now abandoned.

(60) Provisional application No. 62/957,178, filed on Jan. 4, 2020.

(51) Int. Cl.
*A61B 5/11* (2006.01)
*A61B 5/00* (2006.01)

(52) U.S. Cl.
CPC .......... *A61B 5/1126* (2013.01); *A61B 5/6898* (2013.01); *A61B 5/7267* (2013.01); *A61B 5/7275* (2013.01); *A61B 2562/0219* (2013.01)

(58) Field of Classification Search
CPC ................ A61B 5/1126; A61B 5/7264; A61B 2562/0219
See application file for complete search history.

(56) References Cited

U.S. PATENT DOCUMENTS

| | | | |
|---|---|---|---|
| 6,038,488 | A | 3/2000 | Barnes et al. |
| 6,113,237 | A | 9/2000 | Ober et al. |
| 6,152,564 | A | 11/2000 | Ober et al. |
| 6,295,878 | B1 | 10/2001 | Berme |
| 6,354,155 | B1 | 3/2002 | Berme |
| 6,389,883 | B1 | 5/2002 | Berme et al. |
| 6,936,016 | B2 | 8/2005 | Berme et al. |

(Continued)

OTHER PUBLICATIONS

Han et al., "Space-Time Representation of People Based on 3D Skeletal Data: A Review," 2017 (Year: 2017).*

(Continued)

*Primary Examiner* — Daniel L Cerioni
(74) *Attorney, Agent, or Firm* — The Law Office of Patrick F. O'Reilly III, LLC

(57) ABSTRACT

A body sway measurement system is disclosed herein. The body sway measurement system includes an inertial measurement unit or camera configured to generate time series output data for determining one or more parameters indicative of the body sway of a user; and a mobile device or computing device including a data processor, the data processor including at least one hardware component, the data processor being operatively coupled to the inertial measurement unit or camera, the data processor configured to receive the time series output data from the inertial measurement unit or camera, and the data processor and/or a cloud server programmed to process the time series output data to extract movement features including body displacement and/or sway patterns; and determine the one or more parameters indicative of the body sway of the user using a trained neural network.

22 Claims, 7 Drawing Sheets

(56)                References Cited

U.S. PATENT DOCUMENTS

| | | | |
|---|---|---|---|
| 8,181,541 B2 | 5/2012 | Berme | |
| 8,315,822 B2 | 11/2012 | Berme et al. | |
| 8,315,823 B2 | 11/2012 | Berme et al. | |
| D689,388 S | 9/2013 | Berme | |
| D689,389 S | 9/2013 | Berme | |
| 8,543,540 B1 | 9/2013 | Wilson et al. | |
| 8,544,347 B1 | 10/2013 | Berme | |
| 8,643,669 B1 | 2/2014 | Wilson et al. | |
| 8,700,569 B1 | 4/2014 | Wilson et al. | |
| 8,704,855 B1 | 4/2014 | Berme et al. | |
| 8,764,532 B1 | 7/2014 | Berme | |
| 8,847,989 B1 | 9/2014 | Berme et al. | |
| D715,669 S | 10/2014 | Berme | |
| 8,902,249 B1 | 12/2014 | Wilson et al. | |
| 8,915,149 B1 | 12/2014 | Berme | |
| 9,032,817 B2 | 5/2015 | Berme et al. | |
| 9,043,278 B1 | 5/2015 | Wilson et al. | |
| 9,066,667 B1 | 6/2015 | Berme et al. | |
| 9,081,436 B1 | 7/2015 | Berme et al. | |
| 9,168,420 B1 | 10/2015 | Berme et al. | |
| 9,173,596 B1 | 11/2015 | Berme et al. | |
| 9,200,897 B1 | 12/2015 | Wilson et al. | |
| 9,277,857 B1 | 3/2016 | Berme et al. | |
| D755,067 S | 5/2016 | Berme et al. | |
| 9,404,823 B1 | 8/2016 | Berme et al. | |
| 9,414,784 B1 | 8/2016 | Berme et al. | |
| 9,468,370 B1 | 10/2016 | Shearer | |
| 9,517,008 B1 | 12/2016 | Berme et al. | |
| 9,526,443 B1 | 12/2016 | Berme et al. | |
| 9,526,451 B1 | 12/2016 | Berme | |
| 9,558,399 B1 | 1/2017 | Jeka et al. | |
| 9,568,382 B1 | 2/2017 | Berme et al. | |
| 9,622,686 B1 | 4/2017 | Berme et al. | |
| 9,763,604 B1 | 9/2017 | Berme et al. | |
| 9,770,203 B1 | 9/2017 | Berme et al. | |
| 9,778,119 B2 | 10/2017 | Berme et al. | |
| 9,814,430 B1 | 11/2017 | Berme et al. | |
| 9,829,311 B1 | 11/2017 | Wilson et al. | |
| 9,854,997 B1 | 1/2018 | Berme et al. | |
| 9,916,011 B1 | 3/2018 | Berme et al. | |
| 9,927,312 B1 | 3/2018 | Berme et al. | |
| 10,010,248 B1 | 7/2018 | Shearer | |
| 10,010,286 B1 | 7/2018 | Berme et al. | |
| 10,085,676 B1 | 10/2018 | Berme et al. | |
| 10,117,602 B1 | 11/2018 | Berme et al. | |
| 10,126,186 B2 | 11/2018 | Berme et al. | |
| 10,216,262 B1 | 2/2019 | Berme et al. | |
| 10,231,662 B1 | 3/2019 | Berme et al. | |
| 10,264,964 B1 | 4/2019 | Berme et al. | |
| 10,331,324 B1 | 6/2019 | Wilson et al. | |
| 10,342,473 B1 | 7/2019 | Berme et al. | |
| 10,390,736 B1 | 8/2019 | Berme et al. | |
| 10,413,230 B1 | 9/2019 | Berme et al. | |
| 10,463,250 B1 | 11/2019 | Berme et al. | |
| 10,527,508 B2 | 1/2020 | Berme et al. | |
| 10,555,688 B1 | 2/2020 | Berme et al. | |
| 10,646,153 B1 | 5/2020 | Berme et al. | |
| 10,722,114 B1 | 7/2020 | Berme et al. | |
| 10,736,545 B1 | 8/2020 | Berme et al. | |
| 10,765,936 B2 | 9/2020 | Berme et al. | |
| 10,803,990 B1 | 10/2020 | Wilson et al. | |
| 10,853,970 B1 | 12/2020 | Akbas et al. | |
| 10,856,796 B1 | 12/2020 | Berme et al. | |
| 10,860,843 B1 | 12/2020 | Berme et al. | |
| 10,945,599 B1 | 3/2021 | Berme et al. | |
| 10,966,606 B1 | 4/2021 | Berme | |
| 11,033,453 B1 | 6/2021 | Berme et al. | |
| 11,052,288 B1 | 7/2021 | Berme et al. | |
| 11,054,325 B2 | 7/2021 | Berme et al. | |
| 11,074,711 B1 | 7/2021 | Akbas et al. | |
| 11,097,154 B1 | 8/2021 | Berme et al. | |
| 11,158,422 B1 | 10/2021 | Wilson et al. | |
| 11,182,924 B1 | 11/2021 | Akbas et al. | |
| 11,262,231 B1 | 3/2022 | Berme et al. | |
| 11,262,258 B2 | 3/2022 | Berme et al. | |
| 11,301,045 B1 | 4/2022 | Berme et al. | |
| 11,311,209 B1 | 4/2022 | Berme et al. | |
| 11,321,868 B1 | 5/2022 | Akbas et al. | |
| 11,337,606 B1 | 5/2022 | Berme et al. | |
| 11,348,279 B1 | 5/2022 | Akbas et al. | |
| 11,458,362 B1 | 10/2022 | Berme et al. | |
| 11,521,373 B1 | 12/2022 | Akbas et al. | |
| 11,540,744 B1 | 1/2023 | Berme | |
| 11,604,106 B2 | 3/2023 | Berme et al. | |
| 11,631,193 B1 | 4/2023 | Akbas et al. | |
| 11,688,139 B1 | 6/2023 | Karagoz et al. | |
| 11,705,244 B1 | 7/2023 | Berme | |
| 11,712,162 B1 | 8/2023 | Berme et al. | |
| 11,790,536 B1 | 10/2023 | Berme et al. | |
| 11,798,182 B1 | 10/2023 | Karagoz et al. | |
| 11,816,258 B1 | 11/2023 | Berme et al. | |
| 11,826,601 B1 | 11/2023 | Berme | |
| 11,850,078 B1 | 12/2023 | Berme | |
| 11,857,331 B1 | 1/2024 | Berme et al. | |
| 11,865,407 B1 | 1/2024 | Berme et al. | |
| 11,911,147 B1 | 2/2024 | Berme et al. | |
| 2002/0116990 A1* | 8/2002 | Claussen | A61B 5/1122 73/65.01 |
| 2003/0216656 A1 | 11/2003 | Berme et al. | |
| 2007/0208278 A1* | 9/2007 | Kohen-Raz | A61B 5/4023 600/595 |
| 2008/0228110 A1 | 9/2008 | Berme | |
| 2009/0209343 A1 | 8/2009 | Foxlin et al. | |
| 2011/0277562 A1 | 11/2011 | Berme | |
| 2012/0266648 A1 | 10/2012 | Berme et al. | |
| 2012/0271565 A1 | 10/2012 | Berme et al. | |
| 2014/0024972 A1* | 1/2014 | Greene | A61B 5/1038 600/595 |
| 2014/0114213 A1* | 4/2014 | Allison | A61B 5/112 600/595 |
| 2015/0096387 A1 | 4/2015 | Berme et al. | |
| 2015/0374307 A1* | 12/2015 | Nagasaka | A61B 5/7225 702/145 |
| 2016/0245711 A1 | 8/2016 | Berme et al. | |
| 2016/0334288 A1 | 11/2016 | Berme et al. | |
| 2017/0213145 A1 | 7/2017 | Pathak et al. | |
| 2018/0024015 A1 | 1/2018 | Berme et al. | |
| 2018/0218587 A1 | 8/2018 | Wong et al. | |
| 2018/0253152 A1 | 9/2018 | Forsblom et al. | |
| 2019/0008417 A1 | 1/2019 | Mazumder et al. | |
| 2019/0078951 A1 | 3/2019 | Berme et al. | |
| 2019/0282130 A1 | 9/2019 | Dohrmann et al. | |
| 2019/0346280 A1 | 11/2019 | Mutschler et al. | |
| 2020/0139229 A1 | 5/2020 | Berme et al. | |
| 2020/0170510 A1 | 6/2020 | Ferdows et al. | |
| 2020/0205697 A1 | 7/2020 | Zheng et al. | |
| 2020/0405216 A1* | 12/2020 | Matsumura | G16H 20/70 |
| 2020/0408625 A1 | 12/2020 | Berme et al. | |
| 2021/0333163 A1 | 10/2021 | Berme et al. | |
| 2022/0178775 A1 | 6/2022 | Berme et al. | |
| 2023/0027320 A1* | 1/2023 | Pathak | A61B 5/1124 |
| 2023/0083094 A1* | 3/2023 | Watanabe | A61B 5/6803 700/245 |
| 2023/0187041 A1* | 6/2023 | Teterin | G16H 50/20 705/2 |
| 2023/0233158 A1* | 7/2023 | Mahadevan | A61B 5/445 600/301 |
| 2023/0298760 A1* | 9/2023 | Wagner | A61B 5/7275 705/2 |

OTHER PUBLICATIONS

First office action on the merits (Non-Final Rejection) in U.S. Appl. No. 17/141,014, mailed on Mar. 4, 2021.

Second office action on the merits (Final Rejection) in U.S. Appl. No. 17/141,014, mailed on Aug. 11, 2021.

Third office action on the merits (Non-Final Rejection) in U.S. Appl. No. 17/141,014, mailed on Nov. 23, 2021.

Fourth office action on the merits (Final Rejection) in U.S. Appl. No. 17/141,014, mailed on Mar. 9, 2022.

First office action on the merits (Non-Final Rejection) in Appl. No. 17/836, 935, mailed on Jul. 28, 2022.

(56)  References Cited

OTHER PUBLICATIONS

Second office action on the merits (Final Rejection) in U.S. Appl. No. 17/836,935, mailed on Nov. 10, 2022.

Third office action on the merits (Non-Final Rejection) in U.S. Appl. No. 17/836,935, mailed on Feb. 21, 2023.

Fourth office action on the merits (Final Rejection) in U.S. Appl. No. 17/836,935, mailed on Jun. 8, 2023.

Notice of Allowance in U.S. Appl. No. 17/836,935, mailed on Oct. 26, 2023.

* cited by examiner

36

32

34

30

38

30

BODY SWAY MEASUREMENT SYSTEM

CROSS-REFERENCE TO RELATED APPLICATIONS

This is a continuation-in-part of U.S. Nonprovisional patent application Ser. No. 17/836,935, entitled "Body Sway Measurement System", filed on Jun. 9, 2022; which is a continuation-in-part of U.S. Nonprovisional patent application Ser. No. 17/141,014, entitled "Body Sway Measurement System", filed on Jan. 4, 2021; which claims the benefit of U.S. Provisional Patent Application No. 62/957,178, entitled "Body Sway Measurement System", filed on Jan. 4, 2020, the disclosure of each of which is hereby incorporated by reference as if set forth in their entireties herein.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a body sway measurement system. More particularly, the invention relates to a body sway measurement system that utilizes a mobile device or other computing device for determining one or more parameters indicative of the body sway of the user.

2. Background

Patients with damage to the inner ear balance system suffer from lack of head-eye coordination. That means, when these patients move their heads, their vision becomes blurry and their balance function deteriorates accordingly. As one example of a cause, damage to the inner car balance system may occur as a result of the patient sustaining a traumatic brain injury (TBI) or concussion.

In a clinical setting, patients with damaged inner car balance systems may be tested on a balance plate system in order to assess the degree of impairment. However, when an immediate assessment is needed or desired in a non-clinical setting (e.g., when a return-to-play decision needs to be made on the sidelines at a sporting event), it is typically not feasible to utilize a complex balance plate system. In such an application, it is desirable to employ a simpler and less expensive means for assessing the body sway of the subject.

What is needed, therefore, is a body sway measurement system that is capable of casily determining the body sway of a user in a non-clinical setting. Moreover, a body sway measurement system is needed that does not require complex hardware components, such as a complex balance plate. Furthermore, a need exists for a body sway measurement system that can be used to assess a fall risk of a user and/or whether or not the user has potentially sustained a concussion. In addition, a body sway measurement system is needed that can be used to assess other balance problems, such as those common in older adults.

BRIEF SUMMARY OF EMBODIMENTS OF THE INVENTION

Accordingly, the present invention is directed to a body sway measurement system that substantially obviates one or more problems resulting from the limitations and deficiencies of the related art.

In accordance with one or more embodiments of the present invention, there is provided a body sway measurement system that includes an inertial measurement unit or camera configured to generate time series output data for determining one or more parameters indicative of the body sway of a user; and a mobile device including a data processor, the data processor including at least one hardware component, the data processor being operatively coupled to the inertial measurement unit or camera, the data processor configured to receive the time series output data from the inertial measurement unit or camera, and the data processor and/or a cloud server programmed to: (i) process the time series output data to extract movement features including body displacement and/or sway patterns; and (ii) determine the one or more parameters indicative of the body sway of the user using a trained neural network.

In a further embodiment of the present invention, the data processor and/or the cloud server is configured to determine the one or more parameters indicative of the body sway of the user by inputting the time series output data from the inertial measurement unit or camera into the trained neural network, and utilizing the trained neural network to associate the time series output data with a determinate class so as to generate the one or more parameters indicative of the body sway of the user.

In yet a further embodiment, the trained neural network is selected from the group consisting of: (i) a convolutional neural network (CNN), (ii) an inception network, (iii) an echo state network, (iv) and combinations thereof.

In still a further embodiment, the mobile device is selected from the group consisting of: (i) a smartphone, (ii) a tablet computing device, (iii) a laptop computing device, (iv) a smartwatch, and (v) a head-mounted display.

In yet a further embodiment, the one or more parameters indicative of the body sway of the user determined by the data processor of the mobile device and/or the cloud server are selected from the group consisting of: (i) a sway stability score, (ii) a sway angle of the user, (iii) sway coordinates of the user, (iv) a sway envelope of the user, (v) a sway velocity of the user, and (vi) a sway area of the user.

In still a further embodiment, the data processor of the mobile device and/or the cloud server is further configured to determine a fall risk of the user based upon the one or more parameters indicative of the body sway of the user.

In yet a further embodiment, the body sway measurement system comprises the camera configured to generate the time series output data for determining the one or more parameters indicative of the body sway of a user; and the data processor of the mobile device and/or the cloud server is further programmed to determine the sway patterns of the user by tracking a coded target that reflects the body sway of the user.

In still a further embodiment, the mobile device comprises the inertial measurement unit or the camera configured to generate the time series output data for determining the one or more parameters indicative of the body sway of the user; and the data processor of the mobile device and/or the cloud server is configured to determine the one or more parameters indicative of the body sway of the user based upon the time series output data from the inertial measurement unit or the camera.

In yet a further embodiment, the inertial measurement unit or the camera configured to generate the time series output data for determining the one or more parameters indicative of the body sway of the user is located remotely from the mobile device; and the data processor of the mobile device and/or the cloud server is configured to determine the one or more parameters indicative of the body sway of the user based upon the time series output data from the remotely located inertial measurement unit or camera.

In still a further embodiment, the data processor of the mobile device and/or the cloud server is further programmed to: (iii) normalize the time series output data collected from the inertial measurement unit or camera; (iv) perform feature engineering to extract statistical, time-domain, and frequency-domain features from the time series output data collected from the inertial measurement unit, and/or perform feature engineering to extract displacement metrics from the time series output data collected from the camera; and (v) determine the one or more parameters indicative of the body sway of the user based upon the statistical, time-domain, and frequency-domain features extracted from the time series output data collected from the inertial measurement unit, and/or based upon the displacement metrics extracted from the time series output data collected from the camera.

In yet a further embodiment, the one or more parameters indicative of the body sway of the user determined by the data processor of the mobile device and/or the cloud server comprise a sway stability score for the user, and the data processor of the mobile device and/or the cloud server is further programmed to: (iii) calculate the sway stability score for the user based in part on an age of the user; (iv) adjust an influence of the movement features extracted from the time series output data based on the age of the user; and (v) generate a personalized fall risk assessment for the user that accounts for age-related differences in a stability of the user.

In still a further embodiment, the mobile device comprises the inertial measurement unit and the camera configured to generate the time series output data for determining the one or more parameters indicative of the body sway of the user, the inertial measurement unit comprising at least one of an accelerometer configured to detect linear acceleration and a gyroscope configured to detect angular velocity, and the mobile device configured to concurrently collect the time series output data from the camera and the accelerometer and/or the gyroscope of the inertial measurement unit; and the data processor of the mobile device and/or the cloud server is further programmed to: (iii) analyze the time series output data collected from the accelerometer and/or the gyroscope of the inertial measurement unit to extract motion-related features; (iv) analyze the time series output data collected from the camera to extract the movement features; and (v) integrate the motion-related features extracted from the time series output data collected from the accelerometer and/or the gyroscope of the inertial measurement unit with the movement features extracted from the time series output data collected from the camera to determine the one or more parameters indicative of the body sway of the user.

In yet a further embodiment, the time series output data received by the data processor of the mobile device and/or the cloud server comprises synchronized video data from the camera of the mobile device and inertial measurement unit data from the accelerometer and/or the gyroscope of the inertial measurement unit, the video data from the camera including images of a coded target and the inertial measurement unit data from the inertial measurement unit including accelerometer data and/or gyroscope data, the one or more parameters indicative of the body sway of the user determined by the data processor of the mobile device and/or the cloud server comprise a sway stability score for the user, and the data processor and/or the cloud server is further programmed to: (vi) analyze the synchronized video data from the camera and the inertial measurement unit data from the inertial measurement unit by using the trained neural network; (vii) determine, by using the trained neural network, the sway stability score for the user; and (viii) display the sway stability score on a user interface, wherein the sway stability score is indicative of a fall risk of the user.

In still a further embodiment, the time series output data received by the data processor of the mobile device and/or the cloud server comprises sequential and spatial-temporal data, and the data processor and/or the cloud server is further programmed to: (vi) process, by using the trained neural network, the time series output data from the camera and the inertial measurement unit, the trained neural network configured to process the sequential and spatial-temporal data in the time series output data from the camera and the inertial measurement unit; and (vii) train the trained neural network by using a training module that utilizes a training dataset comprising diverse age groups and movement patterns, thereby enabling the trained neural network to be generally and accurately applied to time series output data sets varying across different populations of users.

In yet a further embodiment, the time series output data received by the data processor of the mobile device and/or the cloud server comprises synchronized video data from the camera of the mobile device and inertial measurement unit data from the accelerometer and/or the gyroscope of the inertial measurement unit as the user engages in daily activities, the one or more parameters indicative of the body sway of the user determined by the data processor of the mobile device and/or the cloud server comprise a sway stability score for the user, and the data processor and/or the cloud server is further programmed to: (vi) analyze, by using the trained neural network, the synchronized video data from the camera and the inertial measurement unit data from the inertial measurement unit as the user engages in the daily activities; (vii) update the sway stability score based on the synchronized video data recently received from the camera and the inertial measurement unit data recently received from the inertial measurement unit so as to provide real-time feedback on a fall risk of the user; and (viii) notify the user or one or more caregivers of the user when significant changes occur in the sway stability score that are indicative of an increased fall risk of the user.

In accordance with one or more other embodiments of the present invention, there is provided a body sway measurement system that includes an inertial measurement unit or camera configured to generate time series output data for determining one or more parameters indicative of the body sway of a user; and a computing device including a data processor, the data processor including at least one hardware component, the data processor being operatively coupled to the inertial measurement unit or camera, the data processor configured to receive the time series output data from the inertial measurement unit or camera, and the data processor and/or a cloud server programmed to: (i) process the time series output data to extract movement features including body displacement and/or sway patterns; and (ii) determine the one or more parameters indicative of the body sway of the user using a trained neural network.

In a further embodiment of the present invention, the data processor and/or the cloud server is configured to determine the one or more parameters indicative of the body sway of the user by inputting the time series output data from the inertial measurement unit or camera into the trained neural network, and utilizing the trained neural network to associate the time series output data with a determinate class so as to generate the one or more parameters indicative of the body sway of the user.

In yet a further embodiment, the computing device is selected from the group consisting of: (i) a desktop computing device, (ii) a tower computing device, (iii) a server computing device, (iv) a small-form-factor personal computer, (v) a smartphone, (vi) a tablet computing device, (vii) a laptop computing device, and (viii) a smartwatch.

In still a further embodiment, the body sway measurement system comprises the camera configured to generate the time series output data for determining the one or more parameters indicative of the body sway of a user; and the data processor of the mobile device and/or the cloud server is further programmed to determine the sway patterns of the user by tracking a coded target that reflects the body sway of the user.

In yet a further embodiment, the one or more parameters indicative of the body sway of the user determined by the data processor of the mobile device and/or the cloud server comprise a sway stability score for the user, and the data processor of the mobile device and/or the cloud server is further programmed to: (iii) calculate the sway stability score for the user based in part on an age of the user; (iv) adjust an influence of the movement features extracted from the time series output data based on the age of the user; and (v) generate a personalized fall risk assessment for the user that accounts for age-related differences in a stability of the user.

It is to be understood that the foregoing summary and the following detailed description of the present invention are merely exemplary and explanatory in nature. As such, the foregoing summary and the following detailed description of the invention should not be construed to limit the scope of the appended claims in any sense.

BRIEF DESCRIPTION OF THE SEVERAL
VIEWS OF THE DRAWINGS

The invention will now be described, by way of example, with reference to the accompanying drawings, in which.

Throughout the figures, the same parts are always denoted using the same reference characters so that, as a general rule, they will only be described once.

DETAILED DESCRIPTION OF EMBODIMENTS
OF THE INVENTION

The present invention is described herein, in an exemplary manner, with reference to computer system architecture and exemplary processes carried out by the computer system. In one or more embodiments, the functionality described herein can be implemented by computer system instructions. These computer program instructions may be loaded directly onto an internal data storage device of a computing device (e.g., an internal data storage device of a smartphone or laptop computing device). Alternatively, these computer program instructions could be stored on a portable computer-readable medium (e.g., a flash drive, etc.), and then subsequently loaded onto a computing device such that the instructions can be executed thereby. In other embodiments, these computer program instructions could be embodied in the hardware of the computing device, rather than in the software thereof. It is also possible for the computer program instructions to be embodied in a combination of both the hardware and the software.

This description describes in general form the computer program(s) required to carry out the body sway analysis for a user. Any competent programmer in the field of information technology could develop a system using the description set forth herein.

For the sake of brevity, conventional computer system components, conventional data networking, and conventional software coding will not be described in detail herein. Also, it is to be understood that the connecting lines shown in the block diagram(s) included herein are intended to represent functional relationships and/or operational couplings between the various components. In addition to that which is explicitly depicted, it is to be understood that many alternative or additional functional relationships and/or physical connections may be incorporated in a practical application of the system.

Figure 1:
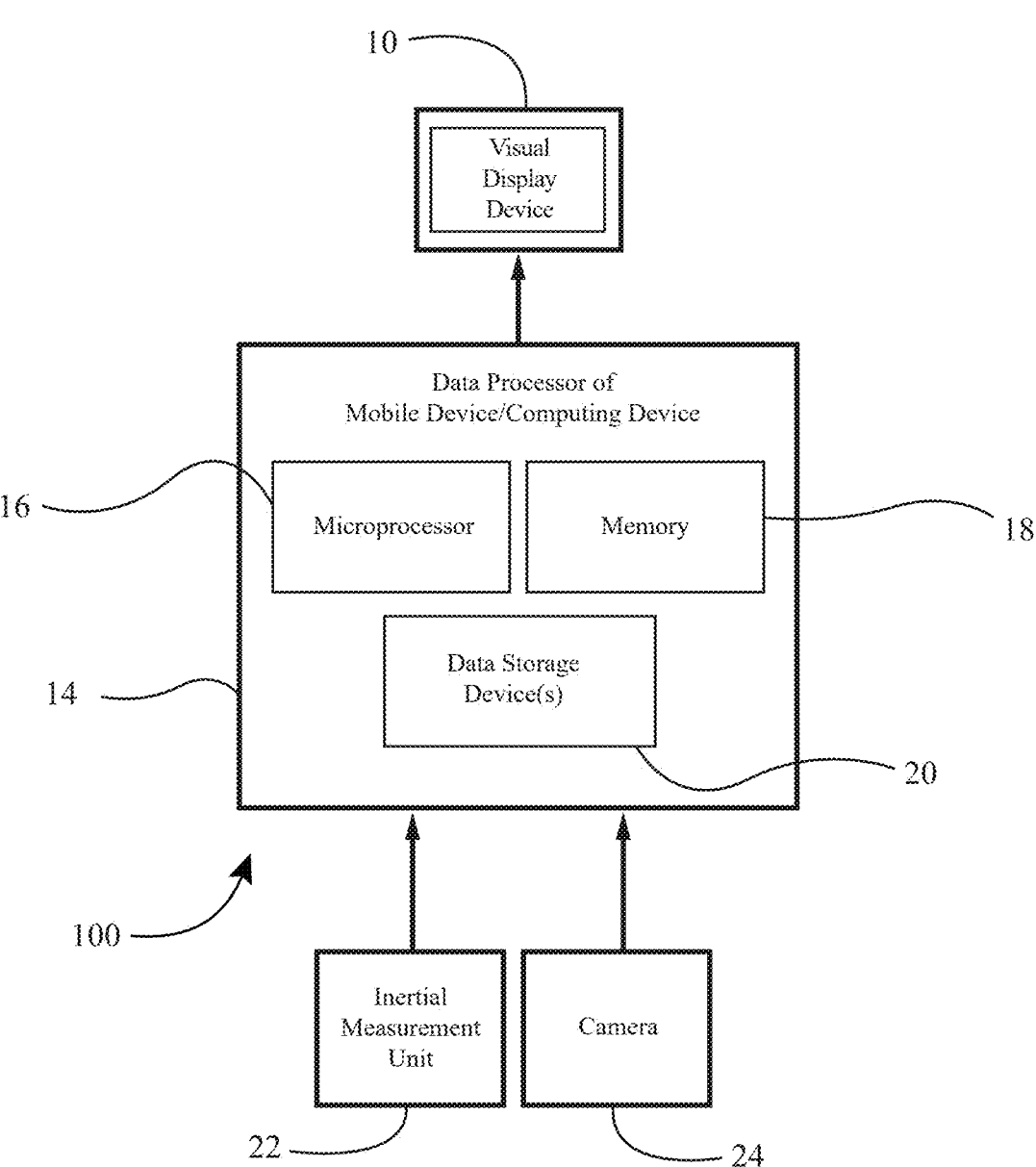
FIG. 1 is a block diagram of constituent components that may be utilized in an illustrative embodiment of the body sway measurement system described herein.

An illustrative embodiment of a body sway measurement system is seen generally at 100 in FIG. 1. In the illustrative embodiment, the body sway measurement system 100 generally comprises a visual display device 10 and a data processor 14 (e.g., a data processor of a computing device, such as a mobile device). Also, as shown in FIG. 1, the body sway measurement system 100 further comprises at least one of an inertial measurement unit 22 and camera 24 operatively coupled to the data processor 14, the inertial measurement unit 22 and/or the camera 24 is configured to generate output data for determining one or more parameters indicative of the body sway of a user. In the illustrative embodiment, the data processor 14 is configured to receive the output data from the inertial measurement unit 22 and/or camera 24, and to determine the one or more parameters indicative of the body sway of the user. In the illustrative embodiment, the inertial measurement unit 22 comprises at least one of an accelerometer configured to detect linear acceleration and a gyroscope configured to detect angular velocity. For example, in the illustrative embodiment, the inertial measurement unit 22 may comprise a 3-axis accelerometer, a 3-axis gyroscope and a 3-axis magnetometer to enable the use of motion fusion algorithms. For the motion fusion algorithms, nine (9) degrees of freedom are needed. In this example, the data processor uses square root formula(s) and/or a principal component analysis (PCA) to determine the sway score of the user from the accelerometer, gyroscope, and magnetometer output data.

In one illustrative embodiment, the mobile device with the data processor 14 is selected from the group consisting of: (i) a smartphone, (ii) a tablet computing device, (iii) a laptop computing device, (iv) a smartwatch, and (v) a head-mounted display. For example, in the illustrative embodiment, the inertial measurement unit 22 and/or camera 24 of the body sway measurement system 100 may comprise the built-in inertial measurement unit and/or camera of a smartphone. In another illustrative embodiment, rather than a mobile computing device, another type of computing device is used. For example, the other type of computing device may be a desktop computing device, a tower computing device, a server computing device, or a small-form-factor personal computer. In yet another illustrative embodiment, the sway of the user may be analyzed by an inertial measurement unit on the chest of the user or by the inertial measurement unit present in a head-mounted display.

Figure 4:
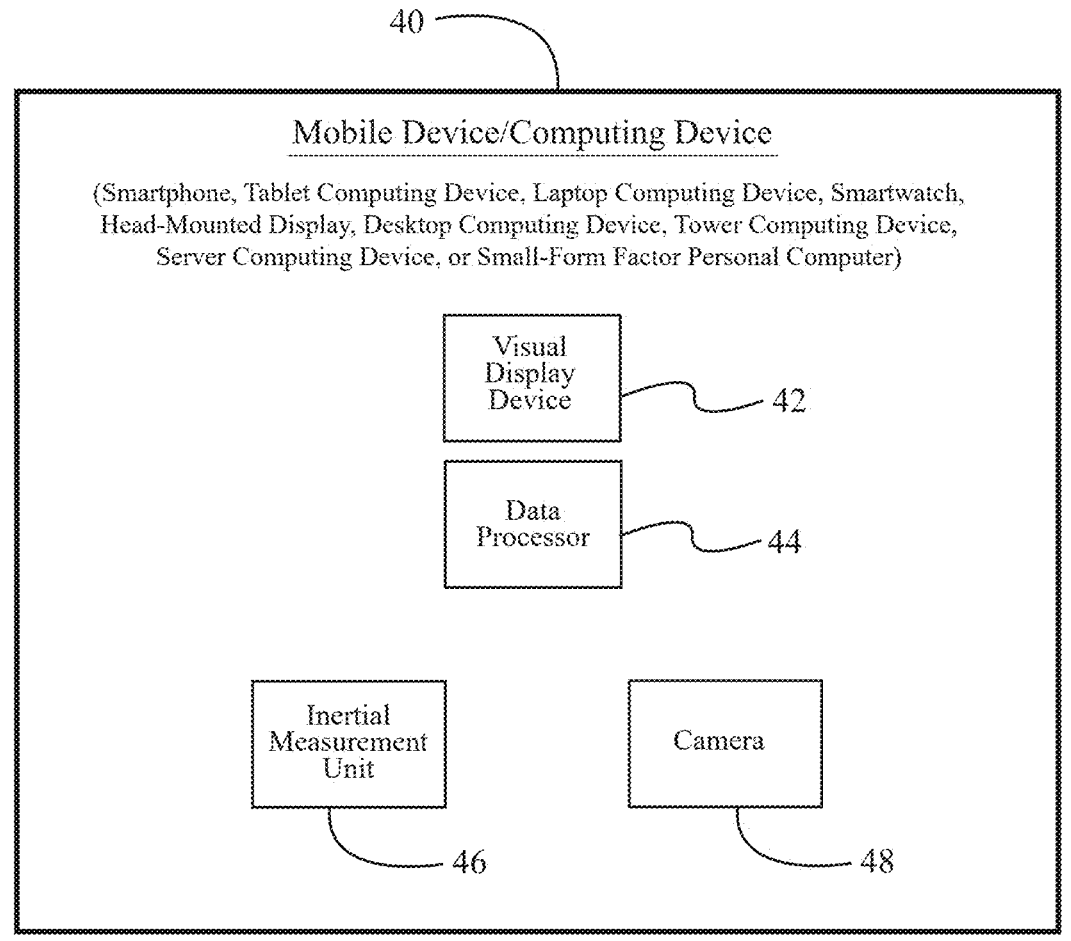
FIG. 4 is a block diagram of constituent components of one illustrative body sway measurement system, where the mobile device or computing device comprises an integral inertial measurement unit and camera.

In FIG. 4, an illustrative body sway measurement system comprising a mobile device or computing device 40 with a built-in inertial measurement unit 46 and a built-in camera 48 is diagrammatically represented. The built-in inertial measurement unit 46 and camera 48 are operatively coupled to the data processor 44 of the mobile device or computing device 40. Also, as shown in FIG. 4, the mobile device or computing device 40 also may include a built-in visual display device 42 (e.g., the touchscreen of a smartphone or the display of a head-mounted display) that is operatively coupled to the data processor 44 of the mobile device or computing device 40.

As shown in the illustrative block diagram of FIG. 1, the data processor 14 (e.g., the data processor 14 of the mobile device or other computing device) of the body sway measurement system 100 comprises a microprocessor 16 for processing data, memory 18 (e.g., random access memory or RAM) for storing data during the processing thereof, and data storage device(s) 20, such as one or more internal solid state drives, external flash drives, or any combination thereof. As shown in FIG. 1, the visual display device 10 is operatively coupled to the data processor 14 such that data is capable of being transferred between these devices (e.g., the visual display device 10 may be a built-in touchscreen user interface of a mobile device).

In the illustrative embodiment, the body sway measurement system 100 is in the form of a mobile sway measurement system for easily performing a sway analysis in a variety of different locations. As described in further detail below, the body sway measurement system 100 may comprise a remote attachable movement sensor (i.e., a remote inertial measurement unit 22) in operative communication with the mobile device or the inertial measurement unit 22 may comprise the built-in inertial measurement unit (IMU)

of the mobile device (e.g., the smartphone). In the illustrative embodiment, the body sway measurement system 100 may provide haptic and auditory feedback for the user based upon the one or sway parameters determined by the data processor 14. As an alternative, the body sway measurement system 100 may comprise an optical motion capture system that utilizes a camera 24 (either the built-in camera of the mobile device or a remote camera) to capture image data for determining the one or more parameters indicative of the body sway of a user. Also, in the illustrative embodiment, camera optical object stabilization may be used to stabilize the recorded image of the camera 24 by varying the optical path to the sensor.

In a first variation of the illustrative embodiment, the mobile device (e.g., the smartphone) comprises the inertial measurement unit 22 configured to generate the output data for determining the one or more parameters indicative of the body sway of the user (i.e., the built-in inertial measurement unit of the smartphone is utilized). In this first variation of the illustrative embodiment, the data processor 14 of the mobile device is configured to determine the one or more parameters indicative of the body sway of a user based upon the output data from the inertial measurement unit 22.

For example, as part of the sway analysis, the inertial measurement unit 22 (i.e., IMU 22) is capable of measuring gravitational and motion components. The gravitational component makes it possible to define a true vertical vector. The body sway is the angle and translation made by the IMU 22 around that true vertical. The calculation for the body sway can be done by a principal component analysis (PCA) to approximate the area of body sway excursion (i.e., the body sway envelope) as follows:

$$\sigma_{xy}^2 = \frac{1}{N-1}\sum_{i=1}^{N}(x_i - \bar{x})(y_i - \bar{y}) \tag{1}$$

$$\tan\theta = \frac{\sigma_{xy}^2}{\sigma_0^2 - \sigma_{yy}^2} \tag{2}$$

where $\theta$ in equation (2) above is the body sway angle. In the illustrative embodiment, the computation of the principal component analysis (PCA) set forth in equation (1) may be computed for each joint of the user.

In a second variation of the illustrative embodiment, the inertial measurement unit 22 that is configured to generate the output data for determining the one or more parameters indicative of the body sway of the user is located remotely from the mobile device. In this second variation of the illustrative embodiment, the data processor 14 of the mobile device is configured to determine the one or more parameters indicative of the body sway of a user based upon the output data from the remotely located inertial measurement unit 22. In the illustrative embodiment, the data processor 14 may be operatively coupled to the remotely located inertial measurement unit 22 by a wireless connection.

In the second variation of the illustrative embodiment, a plurality of inertial measurement units 22 located remotely from the mobile device may be used to track the positions of multiple limbs of the user. For example, a first one of the inertial measurement units 22 may be mounted on the first leg of the user (i.e., a left leg), a second one of the inertial measurement units 22 may be mounted on the second leg of the user (i.e., a right leg), a third one of the inertial measurement units 22 may be mounted on the first arm of the user (i.e., a left arm), and a fourth one of the inertial measurement units 22 may be mounted on the second arm of the user (i.e., a right arm). In this illustrative embodiment, the data processor 14 may use the output data from the inertial measurement units 22 for self-identification and/or intrinsic calibration of the inertial measurement units 22. In particular, the data processor 14 may use the positional coordinates outputted by the inertial measurement units 22 to automatically determine which limb the particular inertial measurement unit 22 is attached to (e.g., based on the positional coordinates outputted by the inertial measurement units 22, the data processor 14 is able to determine the left or right orientation of the leg or arm, the front or back orientation of the leg or arm, and determine whether the inertial measurement unit 22 is located on an arm or a leg). Also, the data processor 14 may use the angular data outputted by the inertial measurement units 22 to automatically determine which limb the particular inertial measurement unit 22 is attached to (e.g., when the inertial measurement unit 22 is attached to an arm, rather than the leg, the angular displacement of the inertial measurement unit 22 will be greater because the arm swing angle is greater). Also, when the user swings his or her arms, the angular displacements of the inertial measurement units 22 attached to the arms will be greater in the forward arm swing direction as compared to the rearward arm swing direction. Similarly, when the user walks or runs, the angular displacements of the inertial measurement units 22 attached to the legs will be greater in the forward direction as compared to the rearward direction. As such, the pattern of movement of the user and/or the positional coordinates outputted by the inertial measurement units 22 may be used for self-identification of the inertial measurement units 22. For example, using the pattern of movement of the user and/or the positional coordinates of the inertial measurement units 22, the data processor 14 may identify a front or back orientation of the inertial measurement unit 22, a left or right orientation of the inertial measurement unit 22, and/or whether the inertial measurement unit 22 is attached to a lower limb or an upper limb of the user.

When the inertial measurement units 22 are being used for the live analysis or streaming analysis of the movement of the user, a pre-calibration routine may be performed by the data processor 14 where the self-identification of the inertial measurement units 22 is performed beforehand. When the output data from the inertial measurement units 22 is processed after data collection (i.e., post-processing of the output data), a dynamic calibration routine may be performed by the data processor 14 where the self-identification of the inertial measurement units 22 is performed during data collection (i.e., on-the-fly calibration).

In the illustrative embodiment, the IMU self-identification process may comprise the following three steps for a pre-calibration routine. First, the user may attach the inertial measurement units 22 to his or her body (i.e., one IMU on each arm and one IMU on each leg). Secondly, the user may start walking or take two or more steps in place to calibrate the inertial measurement units 22. Finally, using a model of the user and IMU quaternion and positional data, the data processor 14 automatically detects the inertial measurement units 22 and self-identifies their locations on the user's right and left arms and the user's right and left legs.

As one example, in the first and second variations of the illustrative embodiment, the data processor of the mobile device or computing device may read a stream of data from the IMU. Then, the data processor may combine data from different axes or can use combined data (x, y, z), i.e., look at motion (displacement and rotation) along the three planes.

After which, the data processor applies a sway algorithm to determine the sway stability score. In this example, the best placement of the IMU is around the CoM of the subject (the waist area), but can be also placed on the individual's head. Also, in this example, x-y plane data can be used to look at the horizontal displacement only. In this example, the IMU can be wired or wireless (i.e., communicate by Bluetooth® or WiFi®). The wireless data transfer rate is slower, but is adequate. Also, in this example, one can run this same x-y-z data stream to a CNN model to process the data instead of using calculated/programmed logic.

In the first and second variations of the illustrative embodiment, where the data processor of the mobile device or computing device reads a stream of data from the IMU, the data processor is configured to receive the time series output data from the inertial measurement unit, and then the data processor and/or a cloud server is configured to determine the one or more parameters indicative of the body sway of the user using a trained neural network. More specifically, the data processor and/or the cloud server is configured to determine the one or more parameters indicative of the body sway of the user by inputting the time series output data from the inertial measurement unit into the trained neural network, and utilizing the trained neural network to associate the time series output data with a determinate class so as to generate the one or more parameters indicative of the body sway of the user. The time series output data for the IMU may comprise accelerometer time series output data (e.g., pitch, roll) and gyroscope data (e.g., pitch, roll, yaw) for a given time duration. In addition, one or more force dimensions may be used in the training and classification of the neural network. As one example, the one or more parameters indicative of the body sway of the user determined by the neural network may comprise a sway stability score defined on a particular scale (e.g., 0-Poor to 9-Excellent). Initially, a dataset for each set of output class is collected and the neural network is trained. The neural network is trained on the IMU data (roll, pitch, yaw, etc.) that is collected. Then, after the training of the network, the neural network outputs a sway stability score (e.g., 0-Poor to 9-Excellent) for a new data input matching the dimensionality of the training input (i.e., during inference). In the illustrative embodiment, a dataset is defined as a collection of pairs (e.g., stream of time series raw IMU output data, score class), which means that to each time series of raw IMU output data is associated a determinate class. Given a dataset, the neural network solves a classification problem by associating to a new IMU data set, with generally the same structure as the other previously classified IMU data sets, the probability that the new IMU data set belongs to a particular one of the classes, according to the features of the previous IMU data sets associated to each class. In the illustrative embodiment, the IMU data set may comprise a univariate time series with one ordered set of real values (e.g., accelerometer pitch data), or a M dimensional multivariate time series consisting of M different univariate time series with the same length (e.g., accelerometer pitch data, accelerometer roll data, gyroscope pitch data, gyroscope roll data, gyroscope yaw data). In the illustrative embodiment, the time series classification problem solved by the neural network is performed on the univariate time series (e.g., accelerometer pitch data) or multivariate time series (e.g., accelerometer pitch data, accelerometer roll data, gyroscope pitch data, gyroscope roll data, gyroscope yaw data).

In the illustrative embodiment, during the training of the neural network, the relationship between the sway stability score and a particular IMU time series data set is determined. For example, during the training of the neural network, the sway stability score may be determined for a particular subject based upon ground truth data from a force plate or balance plate while an IMU data set is being acquired using an IMU, then that particular IMU data set is able to be associated with a particular scale (e.g., 0-Poor to 9-Excellent) of the sway stability score.

In the illustrative embodiment, the trained neural network utilized by the data processor and/or the cloud server may be selected from the group consisting of: (i) a convolutional neural network (CNN), (ii) an inception network, (iii) an echo state network, (iv) and combinations thereof.

In the illustrative embodiment, when the trained neural network comprises a convolutional neural network (CNN), the convolutional neural network (CNN) receives the time series output data as an input, is able to successfully capture the spatial and temporal patterns through application train-able filters, and assigns importance to these patterns using trainable weights. Advantageously, the convolutional neural network (CNN) has the ability to learn filters, rather than requiring the filters to be engineered by hand.

In the illustrative embodiment, when the trained neural network comprises an inception network, the inception network receives the time series output data as an input, and processes the data using inception modules, rather than the convolution layers and pooling layers used by the convolutional neural network (CNN).

In the illustrative embodiment, when the trained neural network comprises an echo state network, the echo state network receives the time series output data as an input, and processes the time series output data using neuron-like nodes which are organized into an input layer, hidden layers, a dimension reduction layer, and an output layer. The echo state network is a type of recurrent neural network where each connection between neurons has a corresponding train-able weight. As one example, the dimension reduction layer can be a tensor principal component analysis (PCA) for multivariate time series data.

In the illustrative embodiment, a principal component analysis (PCA) may be applied on IMU (e.g., roll, pitch, yaw) univariate and multivariate data for dimensionality reduction making "class" identification easier by the CNN or other type of neural network that is utilized. For example, the dimension reduction layer of an echo state network may utilize the PCA for multivariate time series data dimension reduction.

In a third variation of the illustrative embodiment, the mobile device (e.g., the smartphone) comprises the camera 24 configured to generate the output data for determining the one or more parameters indicative of the body sway of the user (i.e., the built-in camera 24 of the smartphone is utilized). For example, the mobile device (e.g., the smartphone) may be attached to the user by means of a strap, and the camera 24 of the mobile device may be focused on a remote stationary target. As the user's body moves due to his or her sway, the position of the remote target changes in the image captured by the camera 24 so that the one or more parameters indicative of the body sway of the user may be determined from the image data of the camera 24. In another variation of the illustrative embodiment, the one or more parameters indicative of the body sway of the user may be determined based upon a combination of the image data captured by the camera 24 of the mobile device and the output data of the inertial measurement unit 22 of the mobile device.

In a fourth variation of the illustrative embodiment, the camera 24 that is configured to generate the output data for determining the one or more parameters indicative of the body sway of the user is located remotely from the mobile device. In this fourth variation of the illustrative embodiment, the data processor 14 of the mobile device is configured to determine the one or more parameters indicative of the body sway of a user based upon the output data from the remotely located camera 24. In the illustrative embodiment, the data processor 14 may be operatively coupled to the remotely located camera 24 by a wireless connection.

In this fourth variation of the illustrative embodiment, the data processor 14 of the mobile device is configured to determine the one or more parameters indicative of the body sway of the user based upon the output data from the camera 24 using pose estimation. For example, as part of the sway analysis, the camera 24 is capable of capturing image data of the user. Then, the data processor 14 receives the image data of the user from the camera 24. After receiving the image data, the data processor 14 may then extract features from the image data for providing inputs to a convolutional neural network (CNN). After this step, the data processor 14 may generate one or more keypoints using a keypoint subnet, and determine one or more poses of the user based upon the position of the keypoints. In one or more embodiments, when a plurality of cameras 24 are used to capture the movement of the user, the data processor 14 may generate one or more volumetric heatmaps using the convolutional neural network, and then apply a maximization function to the one or more volumetric heatmaps to obtain a three dimensional pose data of one or more persons in the scene. In the illustrative embodiment, the data processor 14 may be configured to determine the one or more parameters indicative of the body sway of the user from the aforedescribed pose estimation data. In this fourth variation of the illustrative embodiment, the pose estimation system may comprise the 3D pose estimation system described in U.S. Pat. No. 10,853,970, the entire disclosure of which is incorporated herein by reference.

Figure 6:
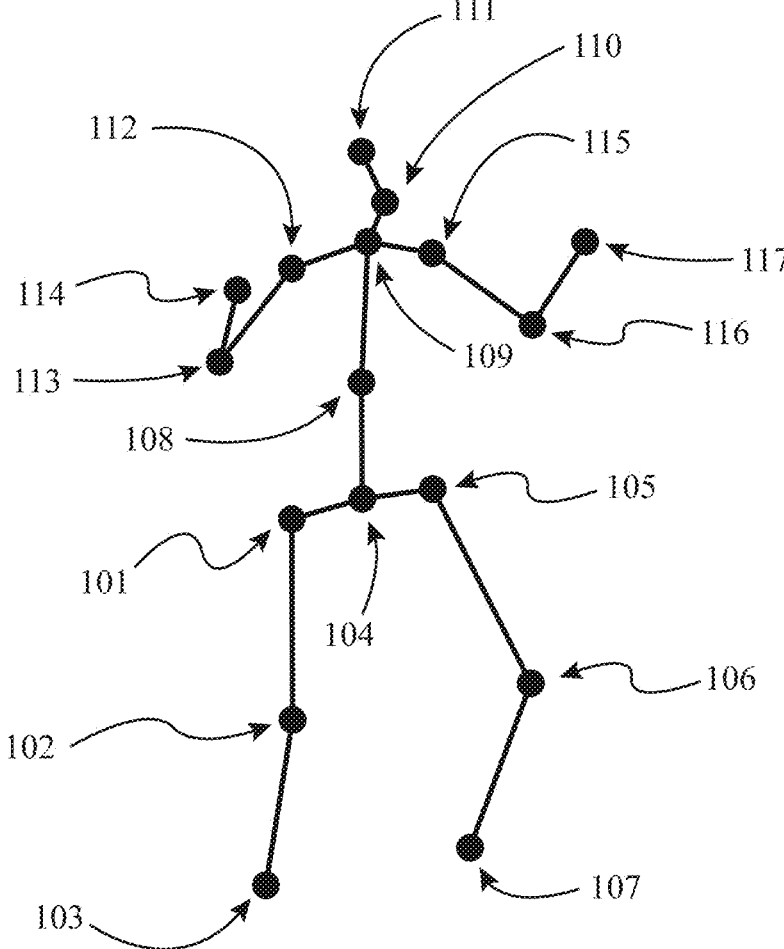
FIG. 6 illustrates keypoint locations for camera-based pose determination performed by the body sway measurement system.

In the fourth variation of the illustrative embodiment, where the data processor of the mobile device or computing device reads a stream of image data from the camera 24, the data processor is configured to receive the time series output data from the camera 24, and then the data processor and/or a cloud server is configured to determine the one or more parameters indicative of the body sway of the user using a trained neural network. More specifically, the data processor and/or the cloud server is configured to determine the one or more parameters indicative of the body sway of the user by inputting the time series output data from the camera 24 into the trained neural network, and utilizing the trained neural network to associate the time series output data with a determinate class so as to generate the one or more parameters indicative of the body sway of the user. The time series output data for the camera 24 may comprise camera-based pose estimated keypoint data (e.g., markered or markerless). FIG. 6 depicts exemplary keypoint locations for a body of a user, which are defined as follows:

101 Right Hip
102 Right Knee
103 Right Foot
104 Bottom Torso
105 Left Hip
106 Left Knee
107 Left Foot
108 Center Torso
109 Upper Torso
110 Neck Base
111 Center Head 112 Right Shoulder
113 Right Elbow
114 Right Hand
115 Left Shoulder
116 Left Elbow
117 Left Hand For input into neural network, one may select a single keypoint on the body such as center torso (108) or a series of keypoints, such as main spine line (111, 110, 109, 108, 104) or the whole body keypoints (101 to 117). As one example, the one or more parameters indicative of the body sway of the user determined by the neural network may comprise a sway stability score or body sway profile/pattern defined on a particular scale (e.g., 0-Poor to 9-Excellent). Initially, a dataset for each set of output class is collected and the neural network is trained. The neural network may be trained on keypoint data collected using markered or markerless motion capture techniques. Then, after the training of the network, the neural network outputs a body sway profile/pattern or sway stability score (e.g., 0-Poor to 9-Excellent) for a new data input matching the dimensionality of the training input (i.e., during inference). In the illustrative embodiment, a dataset is defined as a collection of pairs (e.g., stream of time series keypoint output data, score class), which means that to each time series of keypoint output data is associated a determinate class. Given a dataset, the neural network solves a classification problem by associating to a new keypoint data set, with generally the same structure as the other previously classified keypoint data sets, the probability that the new keypoint data set belongs to a particular one of the classes, according to the features of the previous keypoint data sets associated to each class. In the illustrative embodiment, the keypoint data set may comprise a univariate time series with one ordered set of real values (e.g., single keypoint data), or a M dimensional multivariate time series consisting of M different univariate time series with the same length (e.g., multiple keypoint data). In the illustrative embodiment, the time series classification problem solved by the neural network is performed on the univariate time series (e.g., single keypoint data) or multivariate time series (e.g., multiple keypoint data).

In the illustrative embodiment, during the training of the neural network, the relationship between the sway stability score and a particular kepoint time series data set is determined. For example, during the training of the neural network, the sway stability score may be determined for a particular subject based upon ground truth data from a force plate or balance plate while a keypoint data set is being acquired using the camera 24, then that particular keypoint data set is able to be associated with a particular scale (e.g., 0-Poor to 9-Excellent) of the sway stability score.

In the illustrative embodiment, the trained neural network utilized by the data processor and/or the cloud server may be selected from the group consisting of: (i) a convolutional neural network (CNN), (ii) an inception network, (iii) an echo state network, (iv) and combinations thereof.

Also, in the illustrative embodiment, using the pose estimation described above, the data processor 14 may determine a displacement curve for any of the keypoints of the user (e.g., a displacement curve for the shoulder joint, elbow joint, knee joint, ankle joint, etc.).

As another example, in this fourth variation of the illustrative embodiment, the data processor of the mobile device or computing device may read a streamed sequence of video frames containing the user or subject. Multiple sequential frames (e.g., 30,000 frames spanning 30 seconds) are needed (e.g., 30 seconds to a minute). Then, a trained CNN is used by the data processor to find the center of mass, COM (or center of gravity, CoG) in 3D coordinate space. After which, a sway algorithm is used by the data processor to determine the stability of the subject (i.e., the stability score of the subject). Also, in this example, an additional CNN model may be used to process the 3D COM/CoG data to provide the stability score instead of using calculated/programmed logic. A single camera may be used, but multiple cameras also may be used for more accuracy (i.e., the COM/CoG estimation with a CNN is more accurate with multiple cameras). The camera is generally placed in front of the subject, but the arrangement can vary if multiple cameras are used. Also, with additional training and refinement of the CNN, the stability score can be estimated with a smaller number of frames (e.g., 5 seconds of video data at 60 frames per second).

In the illustrative embodiment, as described above, the one or more parameters indicative of the body sway of the user determined by the neural network may comprise a sway stability score defined on a particular scale (e.g., 0-Poor to 9-Excellent). The neural network may be trained using calculated or collected force data (Fx, Fy, Fz, COM, CoG, etc.). Then, after the training of the network, the neural network outputs a sway stability score (e.g., 0-Poor to 9-Excellent) for a new data input matching the dimensionality of the training input (i.e., during inference).

In the illustrative embodiment, in addition to the sway stability score defined on a particular scale (e.g., 0-Poor to 9-Excellent), other assessment parameters (neural network output classes) for the user may include: (i) fall risk prediction (0-Normal, 1-Fall Risk Above Normal), (ii) fall risk on a scale (0-Normal to 9-High Fall Risk), (iii) normality of gait (0-Normal Gait, 1-Abnormal Gait), and (iv) type of fall risk strategy (0-Hip-Fall-Risk Strategy, 1-Foot-Fall-Risk-Strategy).

Also, in the illustrative embodiment, other sources of input time series data for the neural network may include (i) force plate data (e.g., Fx, Fy, Fz, Mx, My, Mz, CoPx, CoPy, etc.), and (ii) balance plate data (e.g., Fx, Fy, Fz, CoPx, CoPy, etc.). That is, in the illustrative embodiment, one or more force dimensions or their derivatives like CoG (center of gravity)/CoM (Center of Mass)/CoMM (Center of Mass Moments) may be used in the training and classification using the neural networks (e.g., CNNs).

Figure 5:
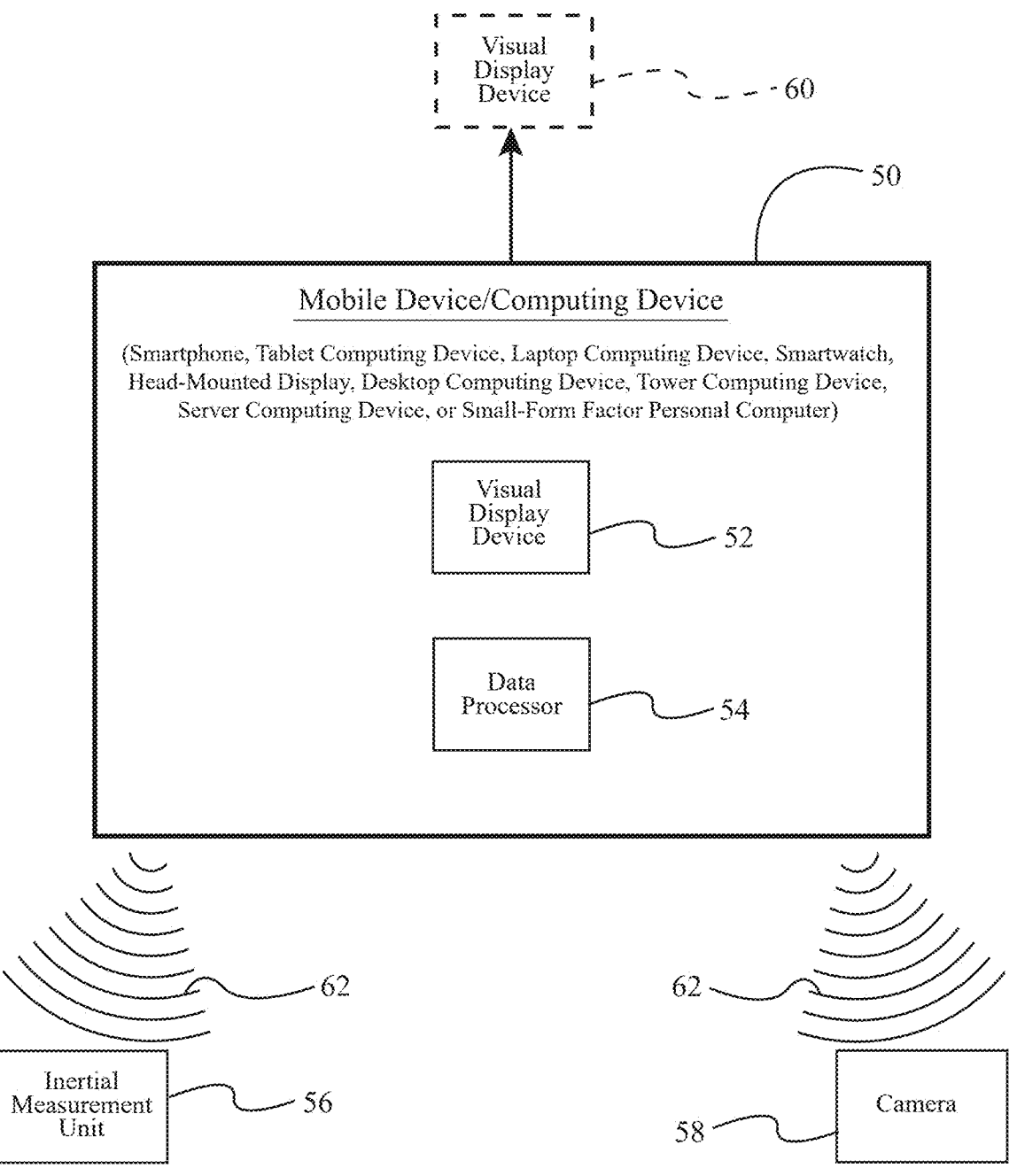
FIG. 5 is a block diagram of constituent components of another illustrative body sway measurement system, where the inertial measurement unit and camera are located remotely from the mobile device or computing device.

In FIG. 5, an illustrative body sway measurement system comprising a mobile device or computing device 50 operatively coupled to a remotely located inertial measurement unit 56 and a remotely located camera 58 by a wireless connection 62 is diagrammatically represented. The remotely located inertial measurement unit 56 and camera 58 are operatively coupled to the data processor 54 of the mobile device or computing device 50 by wireless connection means 62, such as a personal area network (PAN) or local area network (LAN). Also, as shown in FIG. 5, the mobile device or computing device 50 also may include a built-in visual display device 52 (e.g., the touchscreen of a smartphone or the display of a head-mounted display) that is operatively coupled to the data processor 54 of the mobile device or computing device 50. As also shown in FIG. 5, in addition to, or as an alternative to the built-in visual display device 52, the mobile device or computing device 50 may comprises a remotely located visual display device 60.

In the illustrative embodiment, the data acquired by the inertial measurement unit 22 and/or the camera 24 of the mobile device (e.g., the smartphone) may be recorded and processed in a mobile application (i.e., the data may be processed locally on the smartphone). Alternatively, the data acquired by the inertial measurement unit 22 and/or the camera 24 of the mobile device (e.g., the smartphone) may be processed remotely on a cloud server (e.g., the pose estimation may be processed remotely), and then displayed on the mobile device using a mobile application. Also, in the illustrative embodiment, the data acquired may be accessible online throughout a cloud-based system.

In the embodiments where a cloud server is used for processing the data acquired by the inertial measurement unit 22 and/or the camera 24 of the mobile device, the data processor of the mobile device may be used for single instance processing and classification of a test input time series data capture, while cloud processing may be used for further classification of the input sequence with higher dimensional data sets, such as for building, comparing and classifying of the class profile over a period of time (e.g., daily, monthly, or yearly). Advantageously, the cloud processing allows for the comparing of data of different users in real-time distributed in different geographical regions.

In the illustrative embodiment, the mobile device may be programmed (by means of the mobile application) to provide both audio and haptic feedback to the user regarding his or her body sway performance (i.e., an audial or tactile warning may be given to the user if the mobile device determines the body sway of the user is abnormally high, which could potentially result in a fall).

Figure 2:
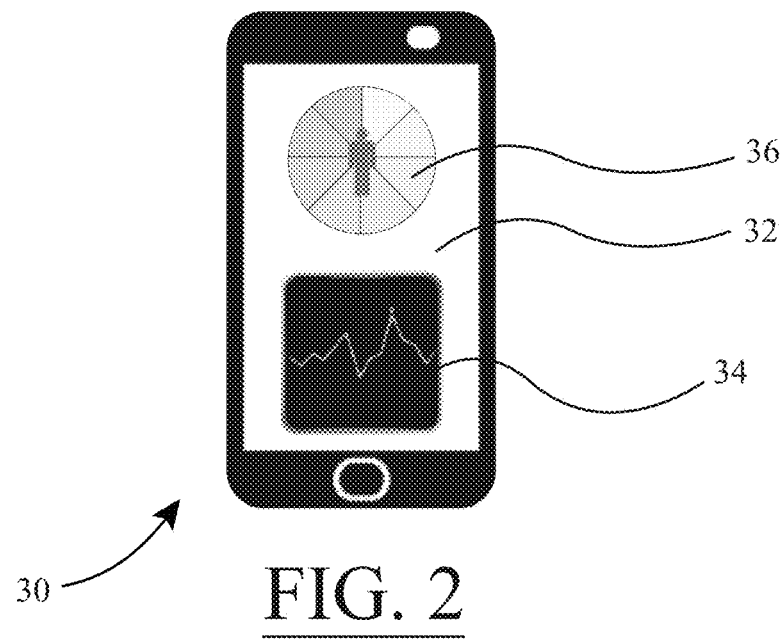
FIG. 2 is a schematic illustration of body sway output information that may be displayed on a smartphone screen of the body sway measurement system.
Figure 3:
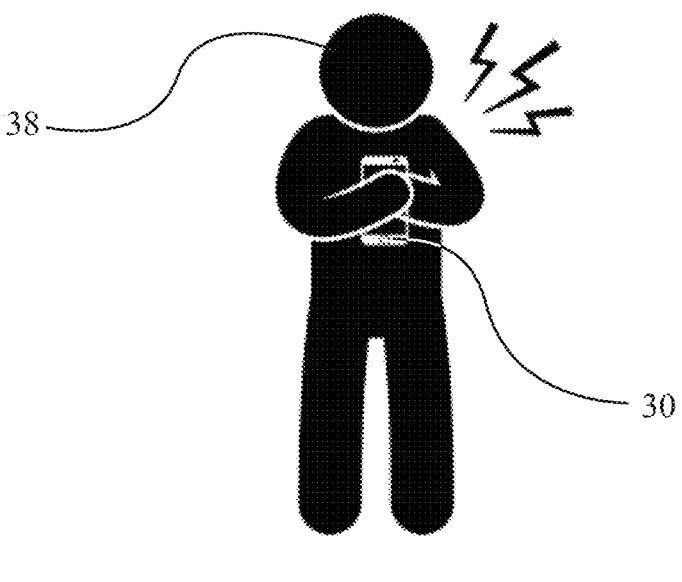
FIG. 3 is a schematic illustration of a user holding a smartphone while the body sway of the user is being measured by the body sway measurement system.

In the illustrative embodiment, the data processor 14 further may be programmed to generate a body sway measurement report with various parameters determined from the output data of the inertial measurement unit 22 and/or the camera 24. For example, the data processor 14 of the mobile device may be programmed to generate and display graphs and other data pertinent to the body sway of the user on the visual display (i.e., touchscreen user interface) of the mobile device (see e.g., FIG. 2). The other data pertinent to the body sway of the user may include body sway parameters, such as: (i) the sway angle of the user, (ii) sway coordinates of the user, (iii) the sway envelope of the user, (iv) a sway velocity of the user, and (v) a sway area of the user. For example, as shown in FIG. 2, the data processor of the smartphone 30 may be programmed to generate and display graphs 34 and other data 36 pertinent to the body sway of the user on the visual display 32. In addition, the data processor 14 of the mobile device may be programmed to track the progress of the user over time (i.e., determine the manner in which the user's body sway changes over time). As explained above, the body sway data may be generated based upon output data from four (4) different sources: (i) an inertial measurement unit 22 of the mobile device, (ii) a remote inertial measurement unit 22, (iii) one or more remote cameras 24 (i.e., one or more remote cameras 24 looking at the user), and (iv) a camera 24 of the mobile device (e.g., when the user 38 is holding the mobile device, such as smartphone 30, as shown in FIG. 3, and the camera 24 of the mobile device is used to determine the movement of the user relative to a fixed object located remotely).

Also, in the illustrative embodiment, the data processor 14 of the mobile device may be further configured to determine a fall risk of the user based upon the one or more parameters indicative of the body sway of a user (e.g., if the sway envelope of the user is outside a predetermined area, then data processor 14 may determine that the user is likely to fall).

In the illustrative embodiment, the body sway measurement system 100 may further comprise a remote visual display device having an output screen (e.g., a remote wall-mounted monitor or television facing the user) operatively coupled to the data processor 14. The remote visual display device may be configured to display at least one manipulatable element (e.g., an airplane) of an interactive game on the output screen so that the at least one manipulatable element is visible to the user. In the illustrative embodiment, the data processor 14 may be programmed to control the movement of the at least one manipulatable element (e.g., an airplane) of the interactive game displayed on the output screen of the visual display device by using the one or more parameters indicative of the body sway of the user (e.g., if the user leans forward, the airplane decreases in altitude, while, if the user leans backward, the airplane increases in altitude). In the exemplary interactive game, the fore/aft leaning of the user could guide the airplane through rings or hoops located at different altitudes in the sky. In the illustrative embodiment, the data processor 14 may be further programmed to determine the fall risk of the user based upon the performance of the user while playing the interactive game (e.g., in the airplane game, the fall risk of the user may increase as the number of rings or hoops missed by the user increases).

In a further embodiment, the body sway measurement system 100 also may include an eye movement tracking device in order to analyze the movement of the user's eyes while the user is focusing on a particular object. For example, if the eye movement tracking device measures erratic eye movements while the user is undergoing a body sway analysis, then the user may have sustained a concussion prior to being tested.

In a further illustrative embodiment, the body sway measurement system 100 may be used for evaluating fall risk in subjects. In this further illustrative embodiment, the body sway measurement system 100 may comprise a mobile device equipped with a camera 24 and an inertial measurement unit (IMU) 22, the camera for recording a coded target and the IMU for capturing motion data; and a data processor 14 and/or a cloud server configured to process both the camera-based data and IMU-based data to identify movement features and calculate a stability score, wherein the stability score predicts the subject's risk of falling. In this further illustrative embodiment, the data processor 14 and/or the cloud server is further configured to: (i) normalize the collected camera-based data and the IMU data; (ii) perform feature engineering to extract statistical, time-domain, and frequency-domain features from the IMU data and displacement metrics from the camera-based data; and (iii) calculate a combined stability score based on an integration of features derived from both the camera and IMU data sources. Also, in this further illustrative embodiment, the data processor 14 and/or the cloud server is further configured to: (i) implement a machine learning model configured to process the integrated camera and IMU data, the model including mechanisms for handling sequential and spatial-temporal data complexities; and (ii) implement a training module for the machine learning model that utilizes a dataset comprising diverse age groups and movement patterns, ensuring the generalizability and accuracy of the machine learning model across different populations.

In this further illustrative embodiment, the body sway measurement system 100 may be used to perform a method for assessing a subject's stability score and fall risk. The method may comprise the steps of: (i) collecting data from a subject using a camera-based system to track a coded target, reflecting the subject's sway; (ii) processing the data to extract movement features including displacement and sway patterns; and (iii) calculating a stability score based on the extracted features, wherein lower scores indicate higher stability and higher scores indicate lower stability. In this further illustrative embodiment, the method may further comprise the steps of: (iv) utilizing an inertial measurement unit (IMU) of a mobile device to collect accelerometer and gyroscope data concurrent with the camera-based data collection; (v) analyzing the accelerometer and gyroscope data of the IMU to extract motion-related features; and (vi) integrating the motion-related features with the camera-based movement features to calculate the stability score for the subject. In this further illustrative embodiment, the calculation of the stability score further comprises: (vii) incorporating the subject's age as a parameter in the stability score calculation; (viii) adjusting the influence of extracted movement features on the stability score based on the subject's age; and (ix) providing a personalized fall risk assessment that accounts for age-related differences in stability.

In this further illustrative embodiment, the body sway measurement system 100 may be used to perform a computer-implemented method for predicting fall risk. The method may comprise the steps of: (i) receiving synchronized video and IMU data from a mobile device, the video data including images of a coded target and the IMU data including three-axis gyroscope and accelerometer readings; (ii) executing a machine learning model on a processor, the model trained to analyze the synchronized data and output a stability score; and (iii) displaying the stability score on a user interface, wherein the score is indicative of the user's fall risk.

In this further illustrative embodiment, the body sway measurement system 100 may be used to perform a method for continuous monitoring and assessment of an individual's fall risk. The method may comprise the steps of: (i) regularly collecting and analyzing data through a mobile device's camera and IMU sensors as the individual engages in daily activities; (ii) updating the individual's stability score based on recent data, providing real-time feedback on fall risk; and (iii) notifying the individual or one or more caregivers of the individual when significant changes in stability scores of the individual indicate increased fall risk.

In this further illustrative embodiment, the body sway measurement system 100 computes a stability score for a user or subject that integrates camera-based tracking, IMU data, and, in some cases, age as a parameter in the computation of the stability score. In this further illustrative embodiment, the computation of the stability score by the body sway measurement system 100 includes the following processes: (i) data processing, (ii) feature extraction, and finally, (iii) the calculation of the stability score itself. Each of these processes will be described in further detail hereinafter.

First, in this further illustrative embodiment, the data processing performed by the body sway measurement system 100 includes data processing related to camera-based tracking and IMU data. With regard to the camera-based tracking, for each frame of the video, the body sway measurement system 100 extracts the position (x, y) of the coded target, which is performed by image processing algorithms capable of identifying and tracking the coded target over time. With regard to IMU data, the body sway measurement system 100 takes IMU data readings from the accelerometer (accelX, accelY, accelZ) and gyroscope (gyroX, gyroY, gyroZ) of the IMU. These readings capture the subject's movements in terms of linear acceleration and angular velocity.

Secondly, in this further illustrative embodiment, the feature extraction performed by the body sway measurement system 100 includes feature extraction from camera data, feature extraction from IMU data, and, in some cases, the incorporation of age of a user. The feature extraction from camera data may include calculating (i) the displacement and (ii) sway path for the user. In this further illustrative embodiment, the displacement of the target in each frame is calculated from a reference position to understand the subject's sway. For example, the displacement may be calculated using the following equation:

$$\text{Displacement}=x_t-x_{ref})^2+(y_t-y_{ref})^2 \qquad (3)$$

Figure 7:
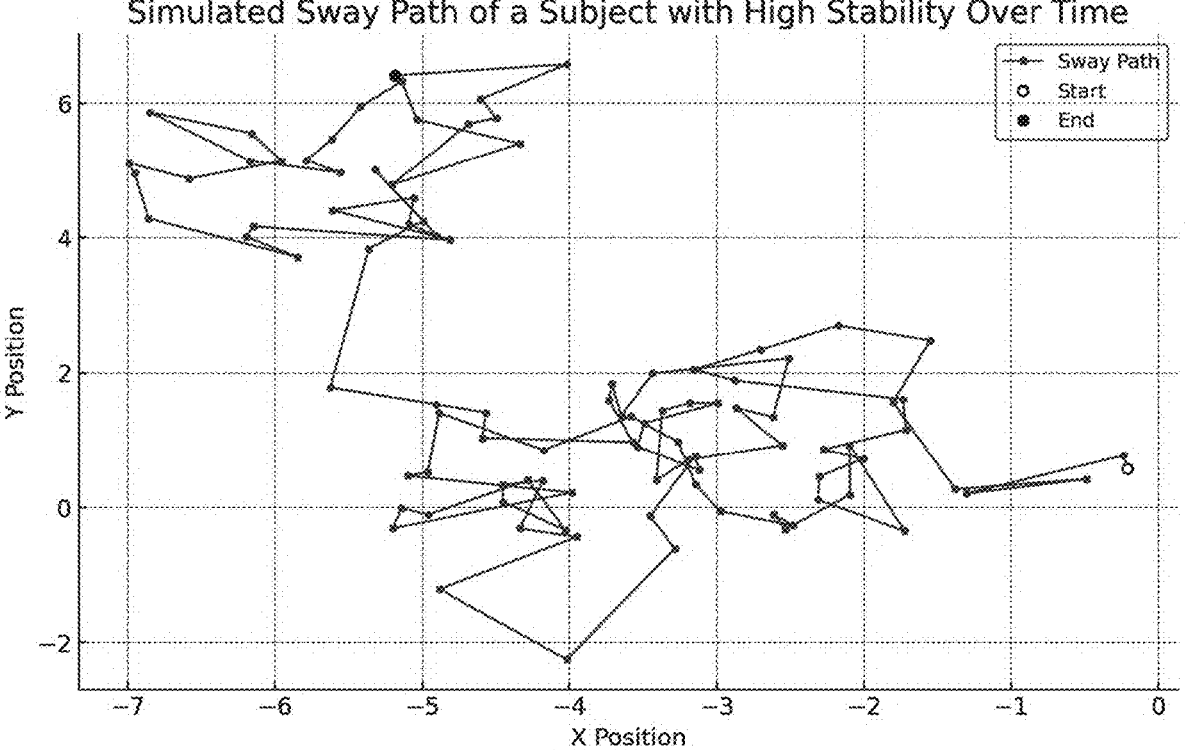
FIG. 7 is a graph illustrating a simulated sway path over time of a subject with high stability, according to an embodiment of the invention.
Figure 8:
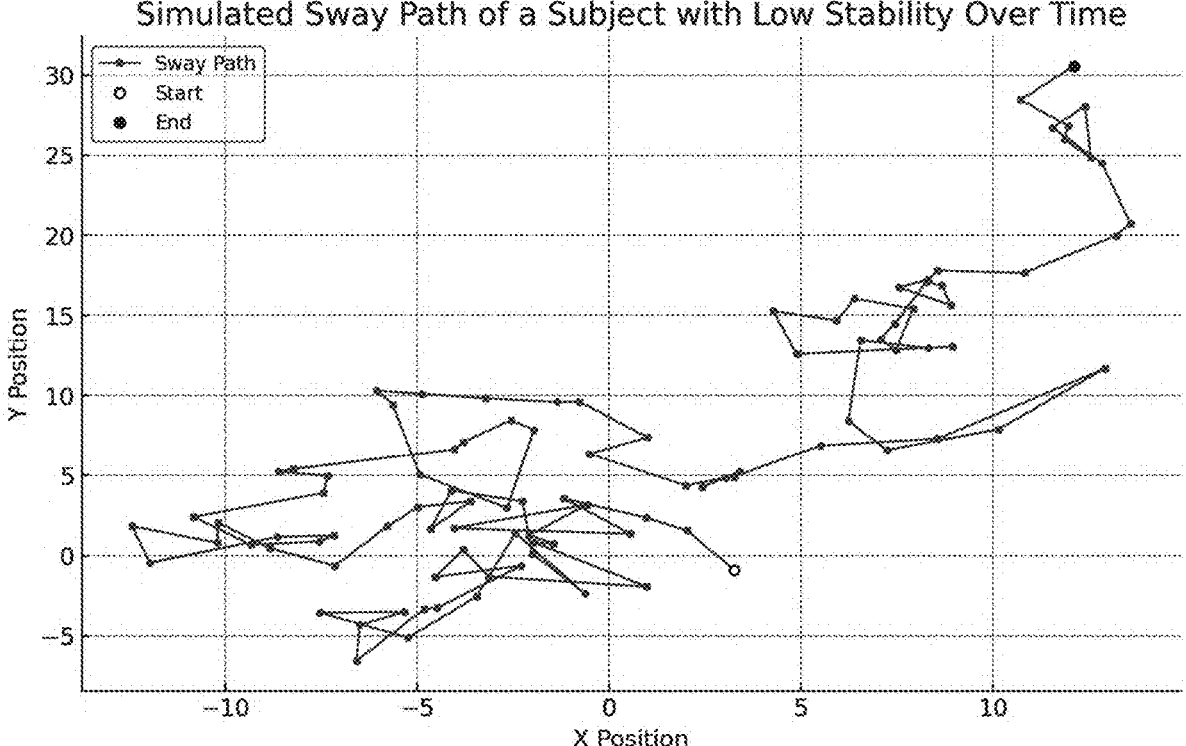
FIG. 8 is a graph illustrating a simulated sway path over time of a subject with low stability, according to an embodiment of the invention.

In this further illustrative embodiment, the total sway path length can also be calculated by summing the distances between consecutive positions over time. For example, a graph illustrating a simulated sway path over time of a subject with high stability is depicted in FIG. 7. As another example, a graph illustrating a simulated sway path over time of a subject with low stability is depicted in FIG. 8. The feature extraction from IMU data may include calculating statistical features, such as mean, variance, and standard deviation, for each of the accelerometer and gyroscope axes to capture the general movement trends. The feature extraction from IMU data may further include calculating frequency domain features by applying a Fast Fourier Transform (FFT) to convert the time-series data into the frequency domain, identifying dominant frequencies that may correspond to sway patterns. In this further illustrative embodiment, the age of the user can be considered directly as a feature or used to modify the influence of other features, recognizing that the physiological impact of sway may vary with age.

Thirdly, in this further illustrative embodiment, the stability score calculation performed by the body sway measurement system 100 includes feature integration, a scoring algorithm, and normalization and scaling. The feature integration may comprise integrating features from both the camera-based tracking and IMU data, possibly weighted by age, to form a comprehensive feature set that captures the subject's stability from multiple dimensions. The scoring algorithm may comprise computing the stability score using a machine learning model trained on labeled data, where labels represent known stability scores. The model may use regression to predict a continuous score or classification for categorized scores. Alternatively, a rule-based system may be used where scores are assigned based on thresholds for certain key features (e.g., maximum displacement, frequency of sway). The normalization and scaling may comprise normalizing the computed stability score to ensure that the score falls within a desired range, often from 1 to 10, where a lower score indicates higher stability (less risk of falling) and a higher score indicates lower stability (higher risk of falling). The computational framework described above for the illustrative embodiment outlines the process from raw data collection through feature extraction to the final computation of a stability score. The integration of camera and IMU data, along with the consideration of age, provides a multi-faceted view of the user's or subject's stability, enhancing the system's ability to accurately assess fall risk.

In this further illustrative embodiment, the body sway measurement system 100 may further comprise: (i) data collection and preprocessing, (ii) feature engineering, (iii) model selection, (iv) training and validation, (v) evaluation and iteration, (vi) deployment and monitoring, and (vii) ethical and privacy considerations in the handling of the data.

The data collection and preprocessing may include hybrid data collection and synchronization and normalization in this further illustrative embodiment. For hybrid data collection, the body sway measurement system 100 simultaneously collects video data for camera-based tracking of a coded target and IMU data (accelerometer and gyroscope readings) from a subject. Additionally, the body sway measurement system 100 may record the subject's age. For synchronization and normalization, the body sway measurement system 100 ensures the video and IMU data are synchronized in time, and the body sway measurement system 100 normalizes the data to have consistent scales and formats, preparing it for analysis. Coded targets may be demarcated as control points in various vision measurement tasks, such as pose estimation, etc. By employing coded targets, matching corresponding image points in multi images may be automatically realized, which greatly improves the efficiency and accuracy of the measurement.

The feature engineering may include camera-based tracking features, IMU data features, and age integration in this further illustrative embodiment. For camera-based tracking features, the body sway measurement system 100 extracts features that quantify the subject's sway, including displacement measurements and sway path characteristics from the video data. For IMU data features, the body sway measurement system 100 derives statistical, time-domain, and frequency-domain features from the accelerometer and gyroscope data to capture movement dynamics. For age integration, the body sway measurement system 100 uses age directly as a feature or to modify other features, recognizing the impact of age on movement characteristics and stability. Feature engineering is a known machine learning technique that leverages data to create new variables that are not present in the training set. Feature engineering can produce new features for both supervised and unsupervised learning, with the goal of simplifying and speeding up data transformations while also enhancing model accuracy.

The model selection may include temporal data handling and multi-input models in this further illustrative embodiment. For temporal data handling, the body sway measurement system 100 utilizes models capable of handling sequential data, such as Long Short-Term Memory networks (LSTMs), Gated Recurrent Units (GRUs), or Convolutional Neural Networks (CNNs) for time-series analysis. For multi-input models, the body sway measurement system 100 utilizes models with multiple input streams that can process and merge and integrate camera and IMU data from both sources, as well as incorporate age effectively.

The training and validation may include dataset splitting, cross-validation, and hyperparameter optimization in this further illustrative embodiment. For dataset splitting, the body sway measurement system 100 divides the collected data into training, validation, and test sets, ensuring a balanced representation of different ages and movement patterns. For cross-validation, the body sway measurement system 100 implements k-fold cross-validation to evaluate the model's generalizability and robustness across unseen data. For hyperparameter optimization, the body sway measurement system 100 systematically tunes the model's hyperparameters to find the optimal configuration for accurate stability score prediction.

The evaluation and iteration may include performance metrics and model refinement in this further illustrative embodiment. For performance metrics, the body sway measurement system 100 may utilize accuracy, precision, recall, F1 score, and confusion matrices for model evaluation, with particular attention to performance across different age groups. For model refinement, the body sway measurement system 100 may, based on evaluation results, iteratively refine the model, feature set, and integration approach to improve predictive accuracy and reliability.

The deployment and monitoring may include real-time assessment and continuous monitoring in this further illustrative embodiment. For real-time assessment, the body sway measurement system 100 may deploy an optimized model within an application or system capable of real-time data processing, providing immediate stability assessments and fall risk predictions. For continuous monitoring, the body sway measurement system 100 may regularly monitor the system's performance in real-world settings, updating the model and algorithms as necessary to maintain accuracy and address any emerging biases.

The ethical and privacy considerations may include data privacy and consent and bias mitigation in this further illustrative embodiment. For data privacy and consent, the body sway measurement system 100 may ensure ethical data collection practices, obtaining consent from subjects, and maintaining the privacy and security of personal data, including age and biometric information. For bias mitigation, the body sway measurement system 100 may actively work to identify and mitigate potential biases, ensuring the system's predictions are equitable across different demographic groups, especially concerning age. In this further illustrative embodiment, the machine learning (ML) pipeline and methodology combines advanced data processing, machine learning modeling, and ethical considerations to develop a robust system for assessing stability and predicting fall risk. The integration of diverse data sources, alongside age, offers a comprehensive and nuanced approach to understanding and quantifying stability, catering to the needs of individuals across various age groups.

In this further illustrative embodiment, temporal data handling by the body sway measurement system 100 in the context of stability score and fall risk assessment is important because the sequential nature of movement data (whether from camera-based tracking or IMU sensors) carries significant information about the subject's stability over time. Models like Long Short-Term Memory networks (LSTMs), Gated Recurrent Units (GRUs), and Convolutional Neural Networks (CNNs) are particularly suited for this task due to their ability to process and learn from sequences. A further explanation of how these models may be used to handle temporal data in the body sway measurement system 100 will be provided hereinafter.

In this further illustrative embodiment, the body sway measurement system 100 may utilize one or more Long Short-Term Memory Networks (LSTMs). With regard to model architecture, LSTMs are a type of Recurrent Neural Network (RNN) designed to overcome the vanishing gradient problem associated with standard RNNs. LSTMs achieve this through a complex architecture that includes memory cells and gates (input, output, and forget gates). With regard to model functionality, LSTMs are capable of learning long-term dependencies by regulating the flow of information through the gates. These gates determine what information is stored, updated, or forgotten at each time step, making LSTMs highly effective for time-series data where current predictions may depend on long-past inputs. With regard to model application, in the context of stability assessment, LSTMs can analyze sequences of (x, y) positions or IMU sensor readings to identify patterns indicative of sway or instability over time.

In this further illustrative embodiment, the body sway measurement system 100 also may utilize one or more Gated Recurrent Units (GRUs). With regard to model architecture, GRUs are similar to LSTMs but with a simplified structure that combines the input and forget gates into a single "update gate" and merges the cell state and hidden state. This simplification can lead to faster training times with comparable performance for certain tasks. With regard to model functionality, like LSTMs, GRUs can maintain information over long sequences but with fewer parameters. GRUs adaptively capture dependencies of different time scales in sequential data, making them suitable for modeling time-series data where the relevance of past information may vary. With regard to model application, GRUs can be employed to process sequential sway data, identifying short-term and long-term movement patterns that contribute to the overall stability score.

In this further illustrative embodiment, the body sway measurement system 100 may further utilize one or more Convolutional Neural Networks (CNNs) for time-series analysis. With regard to model architecture, while CNNs are traditionally associated with image processing, CNNs can also be applied to time-series data. In this context, 1D convolutional layers slide across temporal data, detecting patterns across time steps. With regard to model functionality, CNNs can identify local patterns within sequences, such as specific movements or sway patterns, by applying filters that capture temporal dependencies. This is effective for extracting features from raw time-series data without the need for extensive manual feature engineering. With regard to model application, in stability scoring, CNNs can analyze sequences of movement data, extracting salient features that correlate with different levels of stability or fall risk. When applied to sequences of IMU data, CNNs can detect patterns of acceleration and rotation that signify unstable movements.

In this further illustrative embodiment, any one or all of these models (i.e., Long Short-Term Memory networks (LSTMs), Gated Recurrent Units (GRUs), and Convolutional Neural Networks (CNNs) may be integrated in the machine learning (ML) pipeline. With regard to feature learning, these models can automatically learn features from raw sequential data, reducing the need for manual feature engineering and allowing the system to uncover complex patterns associated with stability and fall risk. With regard to sequential prediction, by processing data sequentially, these models take into account the temporal order of movements, which is important for accurately assessing stability where the timing and sequence of movements are indicative of sway patterns. With regard to model selection, the selection between LSTMs, GRUs, and CNNs can depend on the specific characteristics of the data, computational resources, and the complexity of the temporal patterns in sway and stability data. The selection may also be influenced by the need to integrate temporal data with static inputs, like age. In this further illustrative embodiment, incorporating these models into the ML pipeline of the body sway measurement system 100 for stability score assessment allows for a nuanced understanding of how sequential movement data relates to stability and fall risk, providing a strong foundation for accurate and predictive assessments.

It is readily apparent that the body sway measurement system 100 described above offers numerous advantages and benefits. First, the body sway measurement system 100 is capable of easily determining the body sway of a user in a non-clinical setting. Moreover, the body sway measurement system 100 does not require complex hardware components, such as a complex balance plate. Furthermore, the body sway measurement system 100 is capable of being used to assess a fall risk of a user and/or whether or not the user has potentially sustained a concussion.

While reference is made throughout this disclosure to, for example, "an illustrative embodiment", "one embodiment", a "further embodiment", or a "further illustrative embodiment", it is to be understood that some or all aspects of these various embodiments may be combined with one another as part of an overall embodiment of the invention. That is, any of the features or attributes of the aforedescribed embodiments may be used in combination with any of the other features and attributes of the aforedescribed embodiments as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A body sway measurement system, comprising:
   a camera configured to generate time series output data for determining one or more parameters indicative of the body sway of a user; and
   a mobile device including a data processor, the data processor including at least one hardware component, the data processor being operatively coupled to the camera, the data processor configured to receive the time series output data from the camera, and the data processor and/or a cloud server programmed to:
   process the time series output data to extract movement features including body displacement and/or sway patterns while the mobile device is being worn or held by the user;
   extract displacement metrics from the time series output data collected from the camera focused on a stationary target remote from the user, the displacement metrics including a sway path displacement of the user over time starting from a sway path reference position, the sway path displacement of the user being determined by tracking a position of the stationary target in a plurality of frames of video data acquired by the camera, wherein a greater sway displacement from the sway path reference position is indicative of a lower stability of the user; and
   determine, using a trained neural network, the one or more parameters indicative of the body sway of the user based upon the displacement metrics extracted from the time series output data collected from the camera.

2. The body sway measurement system according to claim 1, wherein the data processor and/or the cloud server is configured to determine the one or more parameters indicative of the body sway of the user by inputting the time series output data from the camera into the trained neural network, and utilizing the trained neural network to associate the time series output data with a determinate class so as to generate the one or more parameters indicative of the body sway of the user.

3. The body sway measurement system according to claim 2, wherein the trained neural network is selected from the group consisting of: (i) a convolutional neural network (CNN), (ii) an inception network, (iii) an echo state network, (iv) and combinations thereof.

4. The body sway measurement system according to claim 1, wherein the mobile device is selected from the group consisting of: (i) a smartphone, (ii) a tablet computing device, (iii) a laptop computing device, (iv) a smartwatch, and (v) a head-mounted display.

5. The body sway measurement system according to claim 1, wherein the one or more parameters indicative of the body sway of the user determined by the data processor of the mobile device and/or the cloud server are selected from the group consisting of: (i) a sway stability score, (ii) a sway angle of the user, (iii) sway coordinates of the user, (iv) a sway envelope of the user, (v) a sway velocity of the user, and (vi) a sway area of the user.

6. The body sway measurement system according to claim 1, wherein the data processor of the mobile device and/or the cloud server is further configured to determine the fall risk of the user based upon the one or more parameters indicative of the body sway of the user.

7. The body sway measurement system according to claim 1, wherein the mobile device comprises the camera configured to generate the time series output data for determining the one or more parameters indicative of the body sway of the user; and wherein the data processor of the mobile device and/or the cloud server is configured to determine the one or more parameters indicative of the body sway of the user based upon the time series output data from the camera.

8. The body sway measurement system according to claim 1, wherein the camera configured to generate the time series output data for determining the one or more parameters indicative of the body sway of the user is located remotely from the mobile device; and wherein the data processor of the mobile device and/or the cloud server is configured to determine the one or more parameters indicative of the body sway of the user based upon the time series output data from the remotely located camera.

9. The body sway measurement system according to claim 1, wherein the data processor of the mobile device and/or the cloud server is further programmed to:

normalize the time series output data collected from the camera.

10. The body sway measurement system according to claim 1, wherein the one or more parameters indicative of the body sway of the user determined by the data processor of the mobile device and/or the cloud server comprise a sway stability score for the user, and the data processor of the mobile device and/or the cloud server is further programmed to:

calculate the sway stability score for the user based in part on an age of the user;

adjust an influence of the movement features extracted from the time series output data based on the age of the user; and generate a personalized fall risk assessment for the user that accounts for age-related differences in a stability of the user.

11. The body sway measurement system according to claim 1, wherein the mobile device further comprises an inertial measurement unit that is configured to generate the time series output data for determining the one or more parameters indicative of the body sway of the user, the inertial measurement unit comprising at least one of an accelerometer and/or a gyroscope, the accelerometer configured to detect linear acceleration and the gyroscope configured to detect angular velocity, and the mobile device configured to concurrently collect the time series output data from the camera and the accelerometer and/or the gyroscope of the inertial measurement unit; and wherein the data processor of the mobile device and/or the cloud server is further programmed to:

analyze the time series output data collected from the accelerometer and/or the gyroscope of the inertial measurement unit to extract motion-related features;

analyze the time series output data collected from the camera to extract the movement features; and integrate the motion-related features extracted from the time series output data collected from the accelerometer and/or the gyroscope of the inertial measurement unit with the movement features extracted from the time series output data collected from the camera to determine the one or more parameters indicative of the body sway of the user.

12. The body sway measurement system according to claim 11, wherein the time series output data received by the data processor of the mobile device and/or the cloud server comprises synchronized video data from the camera of the mobile device and inertial measurement unit data from the accelerometer and/or the gyroscope of the inertial measurement unit, the video data from the camera including images of the stationary target and the inertial measurement unit data from the inertial measurement unit including the accelerometer time series output data and/or the gyroscope time series output data, the one or more parameters indicative of the body sway of the user determined by the data processor of the mobile device and/or the cloud server comprise a sway stability score for the user, and the data processor and/or the cloud server is further programmed to:

analyze the synchronized video data from the camera and the inertial measurement unit data from the inertial measurement unit by using the trained neural network;

determine, by using the trained neural network, the sway stability score for the user; and display the sway stability score on a user interface, wherein the sway stability score is indicative of the fall risk of the user.

13. The body sway measurement system according to claim 11, wherein the time series output data received by the data processor of the mobile device and/or the cloud server comprises sequential and spatial-temporal data, and the data processor and/or the cloud server is further programmed to:

process, by using the trained neural network, the time series output data from the camera and the inertial measurement unit, the trained neural network configured to process the sequential and spatial-temporal data in the time series output data from the camera and the inertial measurement unit; and train the trained neural network by using a training module that utilizes a training dataset comprising diverse age groups and movement patterns, thereby enabling the trained neural network to be generally and accurately applied to time series output data sets varying across different populations of users.

14. The body sway measurement system according to claim 11, wherein the time series output data received by the data processor of the mobile device and/or the cloud server comprises synchronized video data from the camera of the mobile device and inertial measurement unit data from the accelerometer and/or the gyroscope of the inertial measurement unit as the user engages in daily activities, the one or more parameters indicative of the body sway of the user determined by the data processor of the mobile device and/or the cloud server comprise a sway stability score for the user, and the data processor and/or the cloud server is further programmed to:

analyze, by using the trained neural network, the synchronized video data from the camera and the inertial measurement unit data from the inertial measurement unit as the user engages in the daily activities;

update the sway stability score based on the synchronized video data recently received from the camera and the inertial measurement unit data recently received from the inertial measurement unit so as to provide real-time feedback on the fall risk of the user; and notify the user or one or more caregivers of the user when significant changes occur in the sway stability score that are indicative of an increased fall risk of the user.

15. A body sway measurement system, comprising:

a camera configured to generate time series output data for determining one or more parameters indicative of the body sway of a user; and a computing device including a data processor, the data processor including at least one hardware component, the data processor being operatively coupled to the camera, the data processor configured to receive the time series output data from the camera, and the data processor and/or a cloud server programmed to:

process the time series output data to extract movement features including body displacement and/or sway patterns;

extract displacement metrics from the time series output data collected from the camera focused on a stationary target remote from the user, the displacement metrics including a sway path displacement of the user over time starting from a sway path reference position, the sway path displacement of the user being determined by tracking a position of the stationary target in a plurality of frames of video data acquired by the camera, wherein a greater sway displacement from the sway path reference position is indicative of a lower stability of the user; and determine, using a trained neural network, the one or more parameters indicative of the body sway of the user based upon the displacement metrics extracted from the time series output data collected from the camera.

16. The body sway measurement system according to claim 15, wherein the data processor and/or the cloud server is configured to determine the one or more parameters indicative of the body sway of the user by inputting the time series output data from the camera into the trained neural network, and utilizing the trained neural network to associate the time series output data with a determinate class so as to generate the one or more parameters indicative of the body sway of the user.

17. The body sway measurement system according to claim 15, wherein the computing device is selected from the group consisting of: (i) a desktop computing device, (ii) a tower computing device, (iii) a server computing device, (iv) a small-form-factor personal computer, (v) a smartphone, (vi) a tablet computing device, (vii) a laptop computing device, and (viii) a smartwatch.

18. The body sway measurement system according to claim 15, wherein the one or more parameters indicative of the body sway of the user determined by the data processor of the computing device and/or the cloud server comprise a sway stability score for the user, and the data processor of the computing device and/or the cloud server is further programmed to:

calculate the sway stability score for the user based in part on an age of the user;

adjust an influence of the movement features extracted from the time series output data based on the age of the user; and generate a personalized fall risk assessment for the user that accounts for age-related differences in a stability of the user.

19. The body sway measurement system according to claim 11, wherein the data processor of the mobile device and/or the cloud server is further programmed to:

extract frequency-domain features from the time series output data collected from the accelerometer and/or the gyroscope of the inertial measurement unit by applying a Fourier transform (FT);

extract the displacement metrics from the time series output data collected from the camera; and integrate the frequency-domain features extracted from the time series output data collected from the accelerometer and/or the gyroscope of the inertial measurement unit with the displacement metrics extracted from the time series output data collected from the camera to determine the one or more parameters indicative of the body sway of the user.

20. A body sway measurement system, comprising:

an inertial measurement unit and/or camera configured to generate time series output data in a primary domain for determining one or more parameters indicative of the body sway of a user; and a mobile device including at least one of the inertial measurement unit and the camera so as to form a self-contained body sway measurement device, the mobile device further including a data processor, the data processor including at least one hardware component, the data processor being operatively coupled to the inertial measurement unit and/or camera, the data processor configured to receive the time series output data from the inertial measurement unit and/or camera, and the data processor and/or a cloud server programmed to:

process the time series output data to extract movement features including body displacement and/or sway patterns while the mobile device is being worn or held by the user;

extract secondary domain features from the time series output data collected from an accelerometer and/or gyroscope of the inertial measurement unit by applying one or more domain transform operations to accelerometer time series output data and/or gyroscope time series output data so as to identify dominant components corresponding to the sway patterns indicative of a fall risk of the user, and/or extract displacement metrics from the time series output data collected from the camera focused on a stationary target remote from the user, the displacement metrics including a sway path displacement of the user starting from a sway path reference position, wherein a greater sway displacement from the sway path reference position is indicative of a lower stability of the user; and determine, using a trained neural network, the one or more parameters indicative of the body sway of the user based upon the secondary domain features extracted from the time series output data collected from the inertial measurement unit, and/or based upon the displacement metrics extracted from the time series output data collected from the camera.

21. The body sway measurement system according to claim 20, wherein the mobile device comprises the inertial measurement unit and the camera configured to generate the time series output data for determining the one or more parameters indicative of the body sway of the user, the inertial measurement unit comprising at least one of the accelerometer and/or the gyroscope, the accelerometer configured to detect linear acceleration and the gyroscope configured to detect angular velocity, and the mobile device configured to concurrently collect the time series output data from the camera and the accelerometer and/or the gyroscope of the inertial measurement unit; and wherein the data processor of the mobile device and/or the cloud server is further programmed to:

analyze the time series output data collected from the accelerometer and/or the gyroscope of the inertial measurement unit to extract motion-related features;

analyze the time series output data collected from the camera to extract the movement features; and integrate the motion-related features extracted from the time series output data collected from the accelerometer and/or the gyroscope of the inertial measurement unit with the movement features extracted from the time series output data collected from the camera to determine the one or more parameters indicative of the body sway of the user.

22. The body sway measurement system according to claim 21, wherein the data processor of the mobile device and/or the cloud server is further programmed to:

extract the secondary domain features from the time series output data collected from the accelerometer and/or the gyroscope of the inertial measurement unit;

extract the displacement metrics from the time series output data collected from the camera; and integrate the secondary domain features extracted from the time series output data collected from the accelerometer and/or the gyroscope of the inertial measurement unit with the displacement metrics extracted from the time series output data collected from the camera to determine the one or more parameters indicative of the body sway of the user.

* * * * *